United States Patent
Pedrazzini

(10) Patent No.: US 9,785,754 B2
(45) Date of Patent: Oct. 10, 2017

(54) APPARATUS AND PROCEDURE FOR IDENTIFYING PATIENTS AND MARKING CONTAINERS FOR BIOLOGICAL SAMPLES OF SAID PATIENTS

(75) Inventor: Gianandrea Pedrazzini, Paradiso (CH)

(73) Assignee: INPECO HOLDING LTD., Valletta (MT)

( * ) Notice: Subject to any disclaimer, the term of this patent is extended or adjusted under 35 U.S.C. 154(b) by 2165 days.

(21) Appl. No.: 12/599,255

(22) PCT Filed: Apr. 29, 2008

(86) PCT No.: PCT/EP2008/055280
§ 371 (c)(1),
(2), (4) Date: Nov. 6, 2009

(87) PCT Pub. No.: WO2008/135471
PCT Pub. Date: Nov. 13, 2008

(65) Prior Publication Data
US 2011/0145006 A1    Jun. 16, 2011

(30) Foreign Application Priority Data

May 8, 2007    (IT) .............................. MI2007A0927

(51) Int. Cl.
*G06F 19/00*    (2011.01)
*G06Q 50/22*    (2012.01)
(52) U.S. Cl.
CPC ........... *G06F 19/366* (2013.01); *G06Q 50/22* (2013.01)

(58) Field of Classification Search
USPC ........................................................ 705/2, 3
See application file for complete search history.

(56) References Cited

U.S. PATENT DOCUMENTS

| 5,262,049 A | 11/1993 | Ferkany |
| 5,985,215 A | 11/1999 | Sakazume et al. |
| 2001/0039502 A1 | 11/2001 | Case |
| 2009/0048870 A1* | 2/2009 | Godshall et al. ................. 705/3 |

FOREIGN PATENT DOCUMENTS

| DE | 19742160 A1 | 4/1998 |
| WO | WO-01/75769 A2 | 10/2001 |
| WO | WO-2005/111086 A2 | 11/2005 |

* cited by examiner

*Primary Examiner* — Sean K Hunter
(74) *Attorney, Agent, or Firm* — Birch, Stewart, Kolasch & Birch, LLP

(57) ABSTRACT

An apparatus is described for identifying the patient and marking the laboratory test tubes associated with said patient during the sampling of biological material to be analysed, comprising a high-security portable hardware device (1) for processing and storing the patient's data, a device (2) for reading said portable hardware device and for the biometric identification of the patient, a personal computer (4) interacting with an operator and connected to a computer network for exchanging data by means of an application software with a remote means (3) for storing data. Said apparatus also includes a computerised test tube labelling unit (5) comprising a printer (8) for printing bar codes on labels (7) able to receive print commands from said personal computer (4) following a comparison between expected and detected test tubes housed in a positioning and identification device (9) supported by said labelling unit (5).

19 Claims, 8 Drawing Sheets

APPARATUS AND PROCEDURE FOR IDENTIFYING PATIENTS AND MARKING CONTAINERS FOR BIOLOGICAL SAMPLES OF SAID PATIENTS

The present invention concerns an apparatus and a procedure for identifying patients and marking containers for biological samples of said patients.

In almost all cases, a patient's approach to a health facility to obtain services involves the identification of the patient and the relative recording of sensitive and personal data.

This way the health facility intends checking the true identity of the patient and producing any personalised material needed to use the services (e.g. preparation of test tubes for samples).

The most important and historically most problematic stage of this process is the absolute guarantee that the univocal correspondence has occurred between the patient and the products to be analysed (miscellaneous biological materials such as urine, blood, etc. contained in test tubes and other containers).

Patient identification is normally done by personnel of the health facility in charge of patient registration. On the basis of the data and any documents provided by the patient, the operator completes an electronic form entering in the laboratory/hospital database the exams indicated on the prescription form completed by the family doctor. The registration operation ends with the consignment of the labels relating to the requested examinations, of any other necessary expendable materials (e.g. test tubes for samples) and of any form summarising the diagnostic procedures to be completed.

During sampling, the biological material is sampled and associated with the patient either using containers with bar code or bar-coded containers, or with bar code, in the registration stage or applying the bar-coded labels consigned to the patient, always during the registration stage.

Now let us take a detailed look at the stages of the sample process which generally take place in a laboratory.

The patient, after the desk registration stage, moves to the laboratory area dedicated to sampling the biological material, called "sampling point".

The patient is sometimes made to wait his/her turn in a waiting room.

At the sampling point, the patient gives the sampling personnel the containers for the biological samples to be sampled, if necessary already labelled at the time of registration, the labels to be affixed to other containers and any form summarising the diagnostic procedures to be completed.

The biological material is introduced into the specific containers.

At the time of sampling, the operation is performed whereby the biological samples are assigned to the patient from whom said samples have been taken: on each container in fact, the specific label must be affixed that allows recognising the biological sample. Generally speaking, this operation is done manually by the operator, who, once the test tube has been filled, selects the correct label to be affixed on the test tube according to the tests to be carried out on it.

The process described above has various serious drawbacks and "inefficiencies" caused both by human operator and user errors and by systematic errors intrinsic in the process.

Let us take a detailed look.

Risk of "mismatching". The biggest risk that a test laboratory can encounter is an incorrect association of the patient with the sampled biological material and, in a subsequent stage, of the patient with the medical report. In view of the high degree of manual management of the process, it is understandable how a lot of errors can occur due to so-called "mismatching", meaning the switch-over of test tubes and/or analytical results (reports) belonging to different patients. This risk exists and is high in all stages of the process. Imagine, for example, waiting in the waiting room where the switch-over of biological product containers can accidentally occur among different patients. If no further control is made of the patient's identity in the sampling premises, the patient will give the sampling operator test-tubes or labels corresponding to those of another patient. If this should occur, the patient would find him/herself unknowingly with the result/s of tests performed on samples belonging to another patient.

Process inefficiency. The process appears slow and sometimes subject to easy delays. Think for example of when the sampling operator has to affix labels to the test tubes, controlling the correct association with the tests to be performed (distinguishable by the test-tube cap colour).

Production of paper documents. At the counter, all users are provided with a summary sheet with personal details and tests to be performed which will act as an information sheet for the sampling operators. This sheet could go missing or be switched over in the waiting room with that of other users, without such switchover being seen by the sampling operator.

To appreciate how often the problems described above can easily and frequently occur, it must be stressed that a laboratory, albeit of average size, receives hundred (or thousands) of test tubes to be examined every day; each of these test tubes containing biological samples (mother tubes) can give rise, in turn, to a certain number of test tubes (child test tubes) in which the biological material is distributed. Sometimes the same biological samples undergo further control or result-validation tests.

Object of the present invention is to create an apparatus and a registration/sampling/identification procedure for biological material such as to overcome the problems indicated above.

According to the invention, a first object is achieved with an apparatus for identifying the patient and marking the laboratory test tubes associated with said patient in the sampling phase of the biological material to be analysed, characterized by comprising:

a portable hardware device for processing and storing patient's data with a high degree of reliability and able to associate the patient's personal details with his/her biometric details, a device for reading said portable hardware device and for the biometric identification of the patient, a personal computer interacting with an operator and linked to a computer network for exchanging data by means of an applicative software with a remote data storage unit, a computerised test tube labelling unit comprising a printer for printing bar codes on labels suitable for receiving print commands from said personal computer following a comparison made between expected and detected test tubes housed in a positioning and identification device supported by said labelling unit, According to the invention, a second object is achieved with a procedure for identifying the patient and marking the laboratory test tubes associated with said patient in the sampling phase of the biological material to be analysed, characterized by comprising the following phases:

patient authentication by means of a biometric identification device, obtaining on personal computer of patient's personal details by reading a portable hardware high-security date processing and storage device, called biometric identification device producing a code for accessing the information contained in said portable hardware device, obtaining by computer network, from a remote storage device, the list of tests to be performed associated with the identified patient stored at the time of patient registration, obtaining the list of test tubes needed to sample the biological material with coloured cap corresponding to the tests to be performed on each test tube, positioning of the test tube containing biological material on a computerised labelling machine featuring bar code printer, identification of positioned test tube by means of sensors able to identify the dimensional characteristics of the test tubes and the colour of the relevant caps, printing of a label with bar code consistently with the characteristics of the test tube identified by said sensors, test tube labelling.

By bar code is meant a string of characters suitable for being read at a time subsequent to the sampling to provide the operator with information useful for analysing the biological material contained in the test tube.

The computer network can for example be a local intranet network or an internet network.

The labelling unit comprises a rolled tape for supporting the labels to be printed and then affixed to the test tube.

These and other characteristics of the present invention will be made more evident by the following detailed description of an example of its practical realisation illustrated on a non-restrictive basis on the attached drawings, in which.

Figure 1:
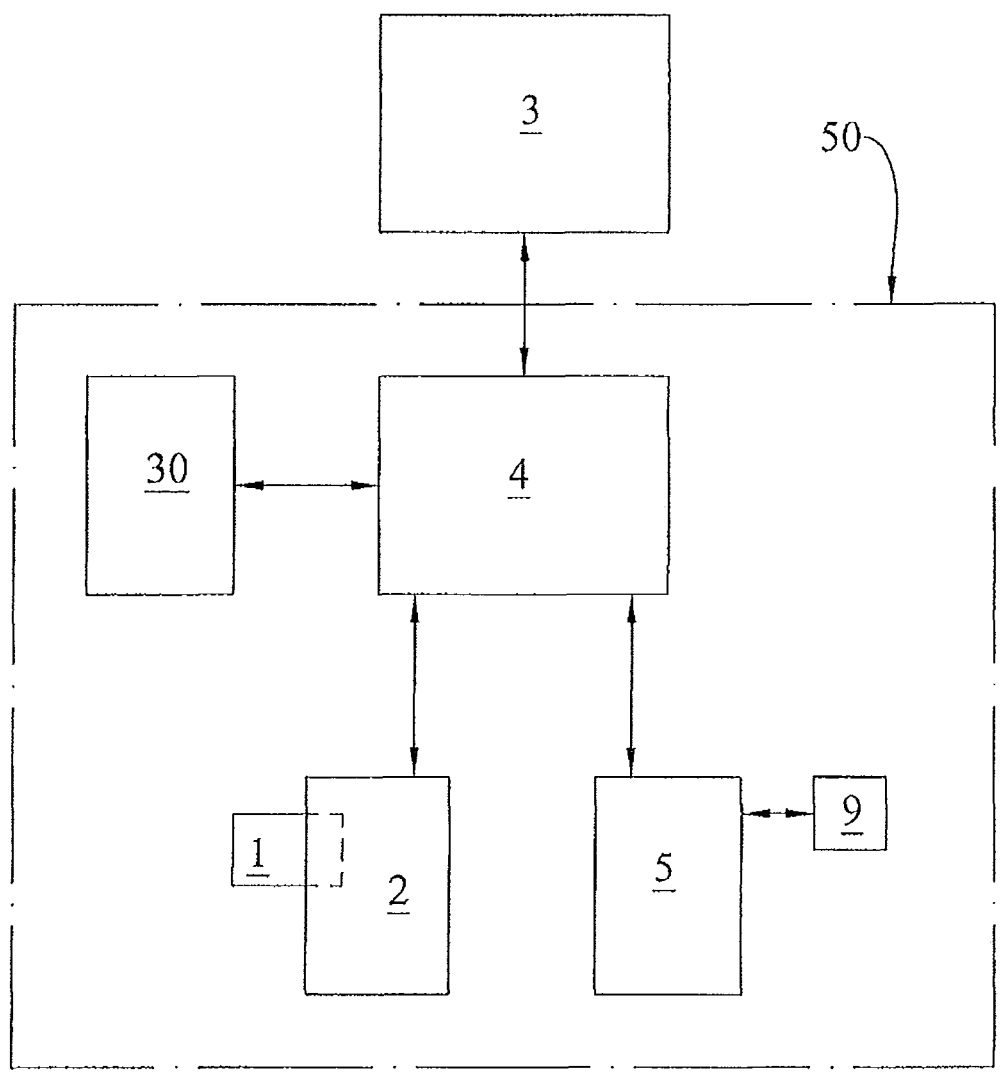
FIG. 1 shows a schematic view of the apparatus according to the present invention.

FIG. 1 shows an apparatus according to the present invention comprising a personal smart card 1 of the patient having a microprocessor with calculation and storage function, and a biometric identification device 2 capable of reading the patient's biometric data and the data contained in the smart card 1.

The smart card 1 contains the patient's personal and biometric details. The personal details are also contained in a database 3 of the laboratory. The biometric data are only stored in the smart card, there being no trace of such data in the database 3. This ensures the preservation of the patient's privacy. In place of the smart card 1 a removable or non-removable bracelet can be envisaged as described in the EP0712525 and EP1292937 or any other portable hardware device having a microprocessor with calculation and storage function.

In the present embodiment, the biometric datum is the print of one or more fingers but it could be the iris, the biometric data of the face, the hand or other physical features of the patient.

The apparatus of FIG. 1 also comprises a personal computer 4 with monitor (preferably a touch-screen) 30 and Internet link to the database 3 of the laboratory, and an automatic or semi-automatic labelling unit 5.

Figure 9:
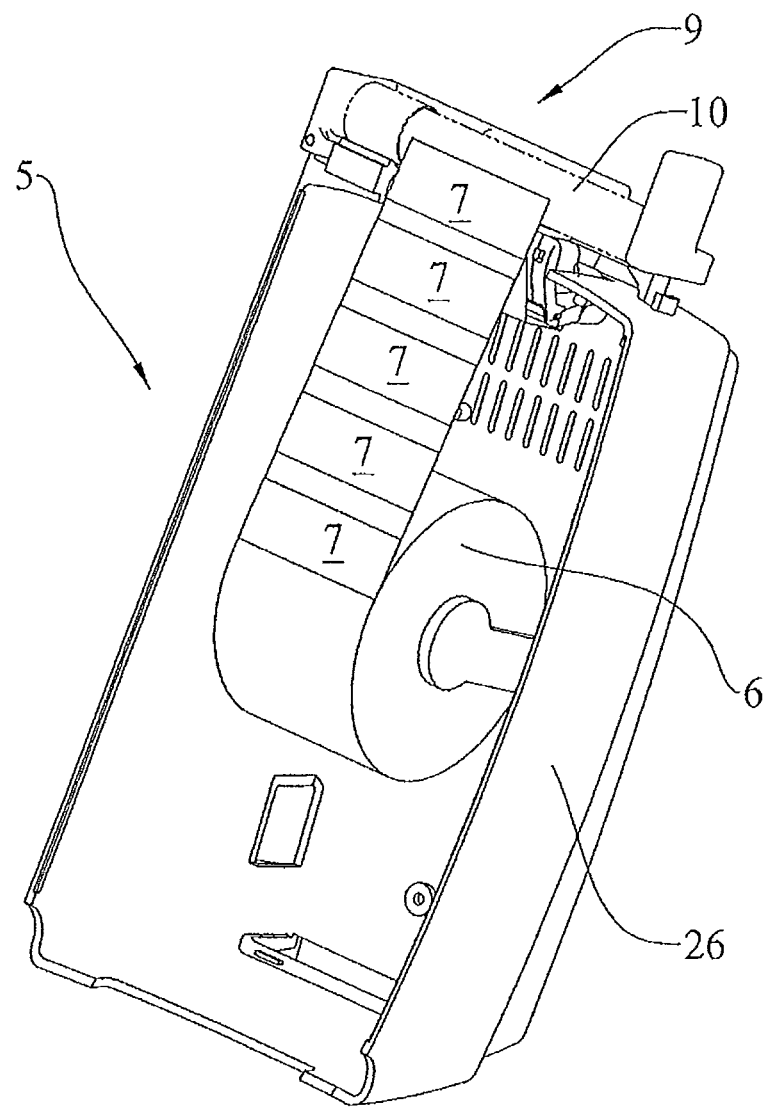
FIG. 9 shows a view in identical perspective to that of FIG. 2 without the cover.
Figure 10:
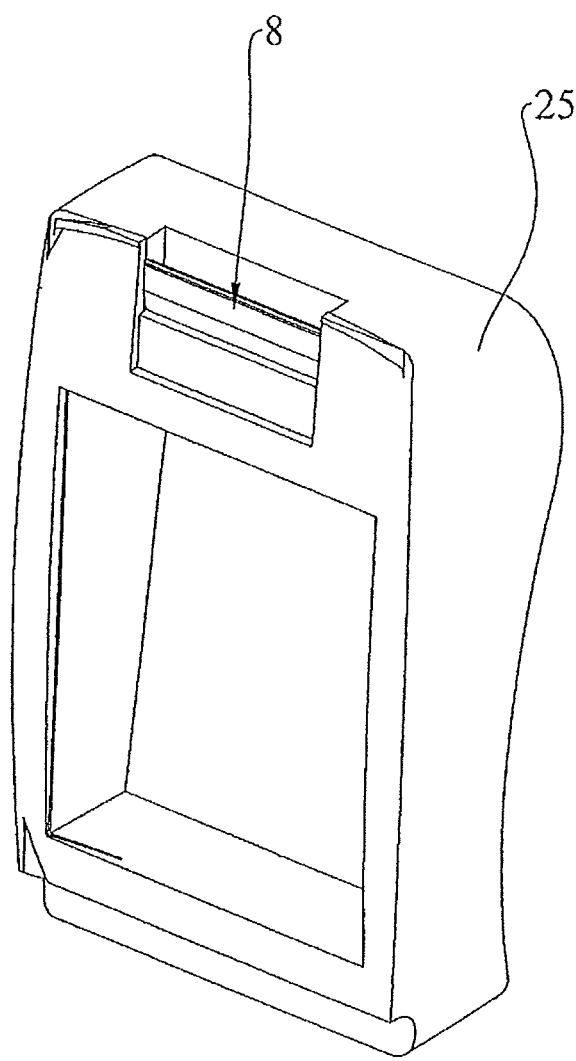
FIG. 10 shows a perspective view of the cover of the labelling unit.

Said labelling unit 5 comprises a rolled tape 6 bearing labels 7 (FIG. 9), a bar-code printer 8 (FIG. 10) and a device 9 for positioning and identifying a test tube or container 10 closed by a coloured cap 11 (FIG. 2) for containing the biological material.

The rolled tape 6 and the printer 8 are contained in a carrying wrap 26 closed with a lid 25.

Figure 4:
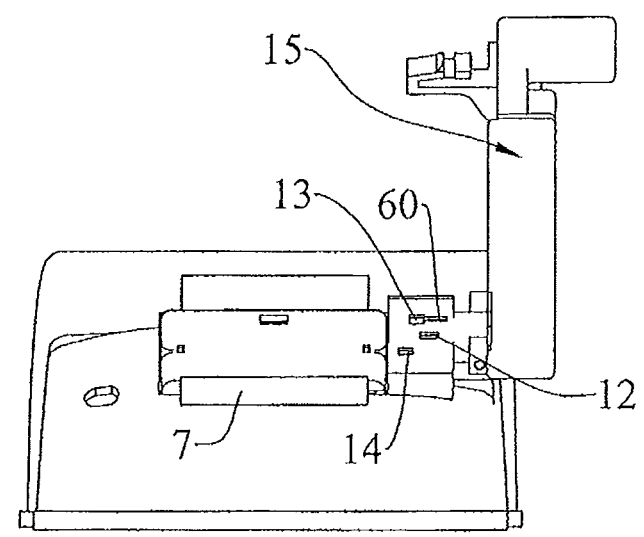
FIG. 4 shows a partial frontal view of the labelling unit in the configuration of FIG. 3.
Figure 5:
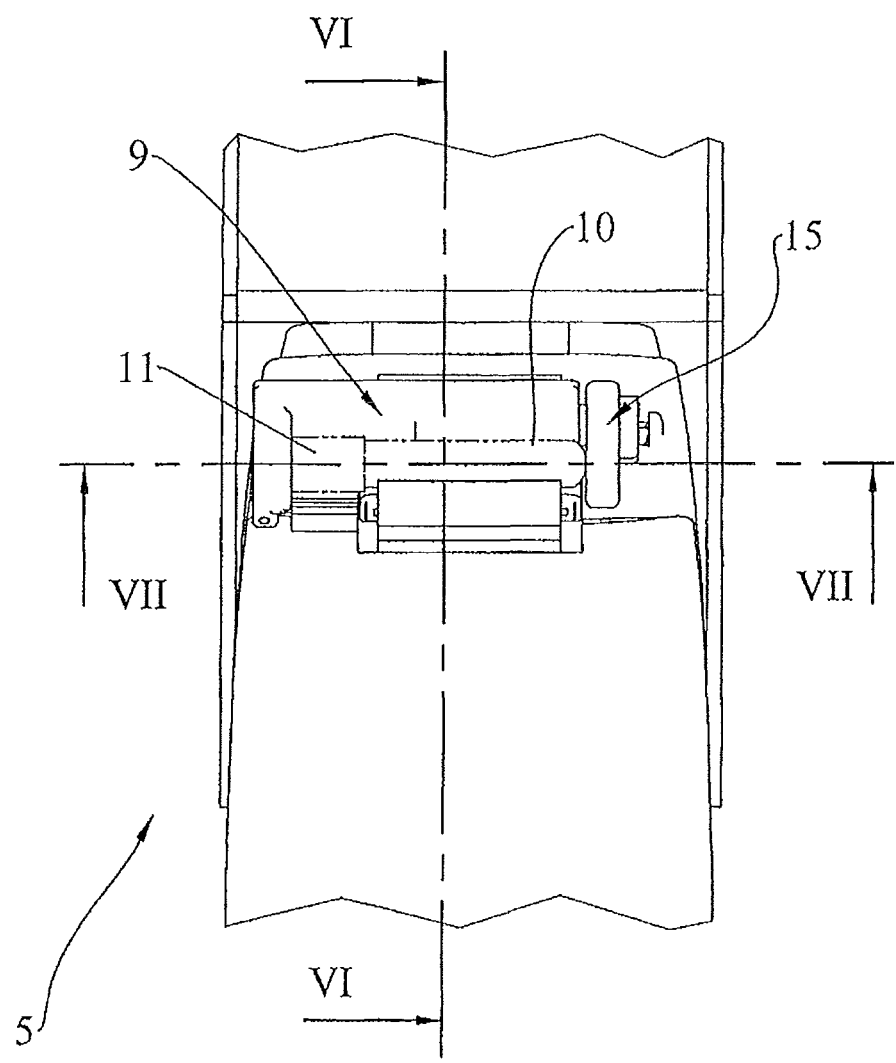
FIG. 5 shows a plan view from above of the labelling unit in the configuration of FIG. 2.
Figure 6:
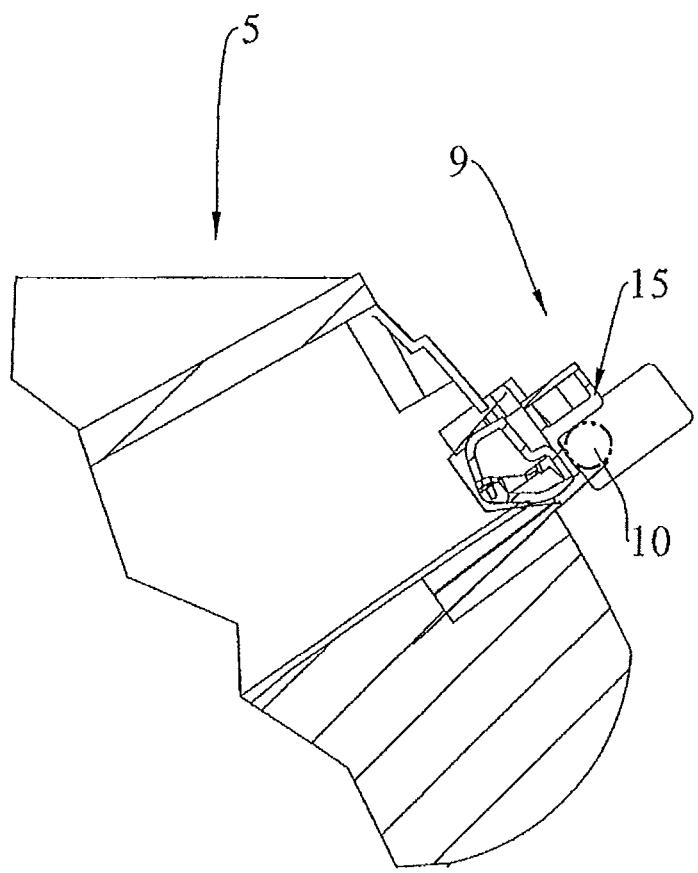
FIG. 6 shows a section view according to tine VI-VI of FIG. 5.

The device 9 comprises a sensor 12 for detecting the presence of the test tube 10, a colour sensor 13 for detecting the colour of the cap 11, and a length sensor 14 for detecting the length of the test tube 10 (FIG. 4).

The sensors 12 and 14 are of the infra-red reflection type, while the sensor 13 is a chip made up of a colour converter consisting of four arrays of sixteen photodiodes complete with a colour filter RGB (Red-Green-Blue) respectively.

Figure 7:
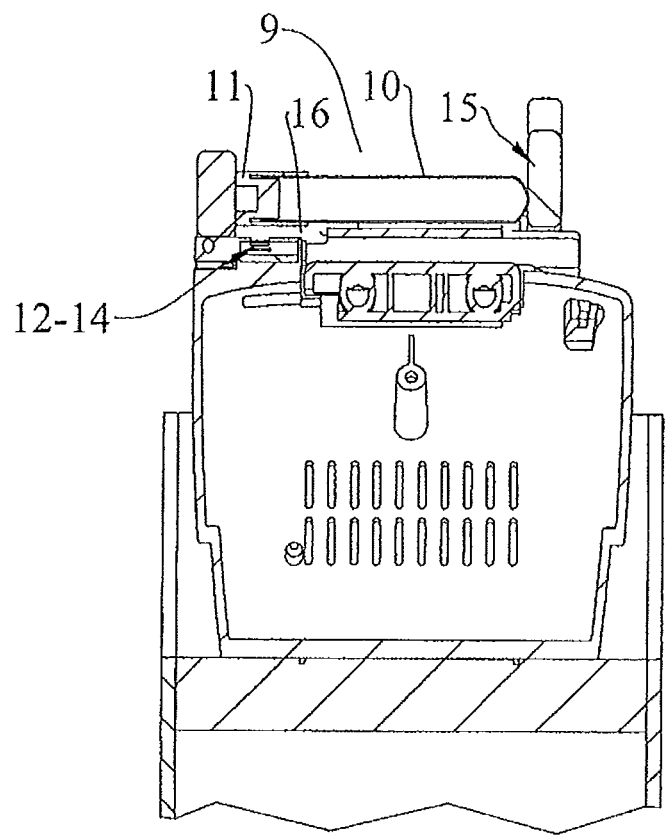
FIG. 7 shows a section view according to line VII-VII of FIG. 5.
Figure 8:
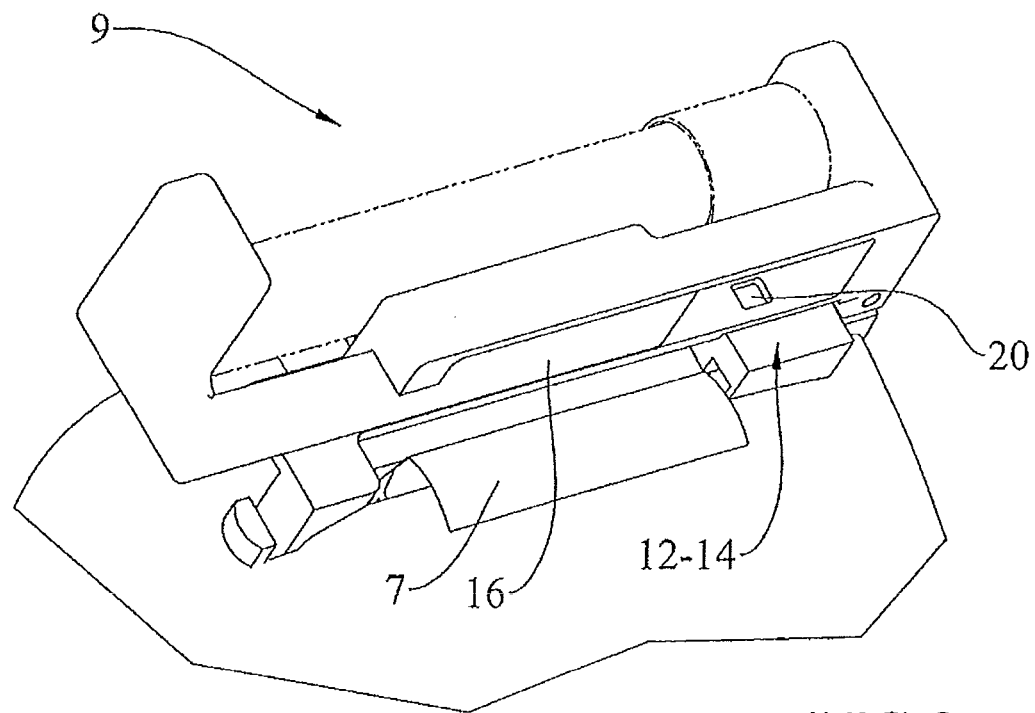
FIG. 8 shows an enlarged perspective view of the device for positioning and identifying the test tube.

The test tube 10 is supported by a housing 15 (FIGS. 2 and 7) having an extensible portion 16 (FIGS. 7 and 8) to adapt to test tubes 10 of different length.

Figure 2:
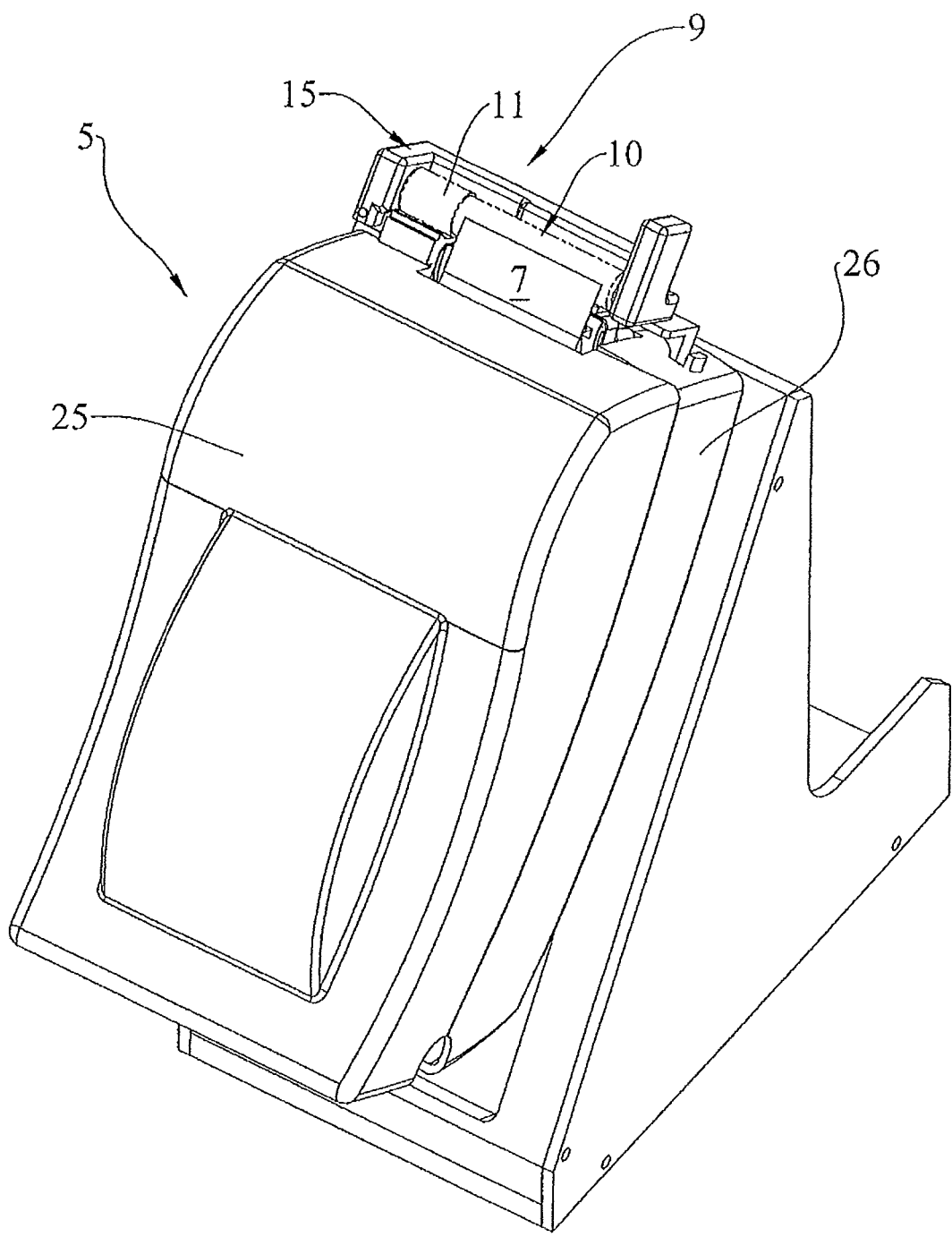
FIG. 2 shows a perspective view of the labelling unit.
Figure 3:
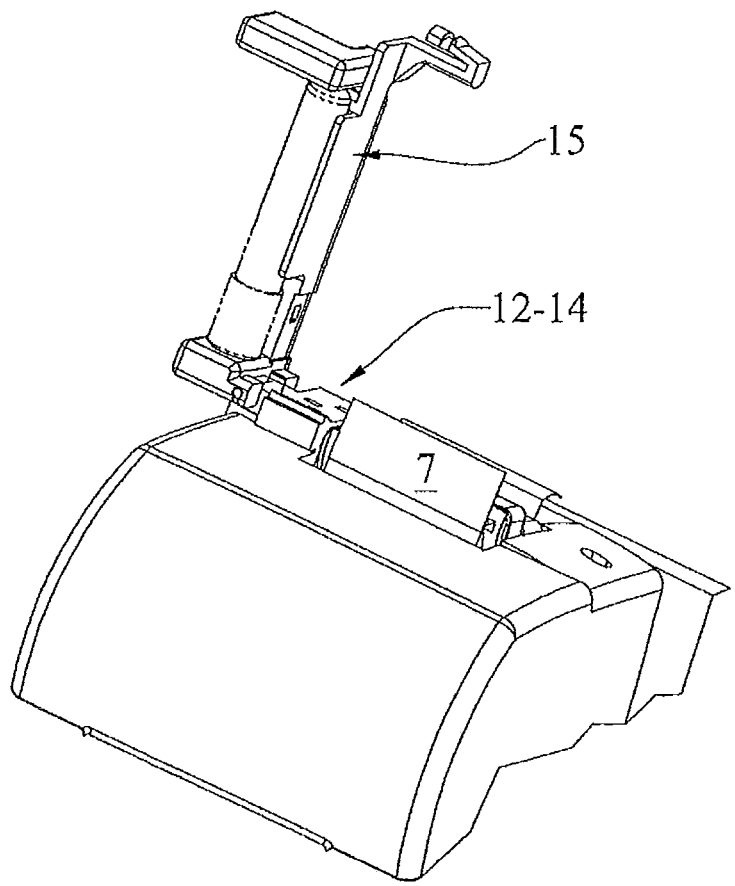
FIG. 3 shows a partial view in perspective similar to that of FIG. 2 with the device for positioning and identifying the test tubes to be labelled in open position to allow loading the rolled tape supporting the labels.

Said housing 15 can be turned by about 90° between a replacement and loading position of the rolled tape 6 (FIG. 3) and an identification/labelling position of the test tube 10 (FIG. 2).

All the component parts of the apparatus described above are connected to a local computer network 50 (intranet) except for the database 3 which is external (remote).

Now let us take a detailed look at the sampling phase and patient-biological material association phase of a laboratory using the biometric identification apparatus backed by smart card 1 and semi-automatic labelling unit 5 of test tubes 10 as described above.

Upstream of this procedure is a first phase of creating and assigning to the patient of the smart card 1 with his/her personal and biometric data (print/s or other biometric data).

After the phase described above (once only) the patient who has received a prescription from his/her doctor goes to the laboratory check-in to make the "data entry" of the prescription if this has not already arrived via computer.

In the event of the doctor having a computer link with the booking centre (CUP), the patient can avoid having to queue at the Laboratory/Hospital check-in and can go directly to the sampling point. When his/her turn comes, the patient positively identifies him/herself by presenting the smart card 1 certifying the personal and clinical data with his/her biometric data. If the biometric data coincides with those on the smart card 1 (positive patient certification), the application, meaning the software installed on the personal computer 4 of the sampling point guides the operator through a correct sampling procedure of the biological samples of the patient.

In other words, the system, after ascertaining the correct identification of the patient by using the smart card 1 provides the application with the patient's personal details. The application interrogates the database 3 of the laboratory to extract the list of tests to be performed (entered in the database 3 during the check-in phase) which are associated with the patient. Once the list of tests has been obtained, the application displays the following data on the touch screen 30:

list of tests to be performed,
according to the number and type of tests to be performed, number and type (differentiated by dimension and colour of the cap) of test tubes 10 expected to be filled with biological material,
to each test on the list is associated the colour of the cap which the test tube must have and its dimension (high or low),
some of the patient's personal details.

Once this information has been obtained and the sample has been taken, the operator positions the test tube 10 filled with biological material in the specific housing 15 installed on the labelling unit 5. By means of the sensors 12-14 featured on the semi-automatic labelling unit 5, the following readings are taken on the test tube 10.

Reflexive and infra-red presence reading by means of the presence sensor 12. A diode emits continuous infra-red radiation which is reflected towards a phototransistor by the presence of any objects placed in the immediate vicinity of the sensor. In this specific case, the sensor detects the presence of the cap 11 of the test tube 10 when this is fitted in the housing 15.

Colour reading. By means of the colour sensor 13, measurements are taken of the intensity of the colour components RGB (Red-Green-Blue) present in the light read, as well as a measurement of the intensity of the light read in general. In our case, the colour sensor 13 reads the colour of the cap 11 of the test tune 10 when this is fitted in the housing 15. The reliability of the colour reading is ensured by a lighting sub-apparatus consisting of a LED 60 that emits white light; this way the target is always lit up in a uniform manner, thereby minimising the colour alterations read by the sensor as a result of changes in environmental conditions.

Length reading. The apparatus features a length sensor 14 based on a reflexive infra-red sensor. The emitting diode emits continuous infra-red radiation which is reflected towards the phototransistor by the presence of any objects placed in the immediate vicinity of the sensor. In this specific case, the sensor 14 looks onto a sliding window 20 in the base of the housing 15 of the test tube 10. The presence of a short test tube 10 leaves the window 20 closed, and the light is therefore reflected, when the test tube 10 is long the window 20 opens, and the light emitted by the photodiode is no longer reflected.

The test-tube presence data acquired by the presence sensor 12 is sent to the application in operation, and this prepares to receive the subsequent data.

The colour and length data describing the test tube positioned in the housing 15 of the labelling unit 5 are compared with the list of expected test tubes.

In case of discrepancy, a message appears on the screen indicating the test tube does not correspond to the listed test tubes and the label 7 is not produced.

In case of correspondence with one of the test tubes expected by the apparatus, the application sends a printing confirmation message to the application resident on the labelling unit.

The printer 8 produces a label with bar code containing the information needed to identify the sample of biological material, and provide a number of details useful to the operators, such as, for example, the person to which the sample belongs (patient), the tests to be performed and the physical characteristics of the test tube identified by the apparatus before the labelling phase.

The label supplied by the labelling unit is affixed to the test tube by rotating this on its own axis. In the present embodiment, this operation is manual (hence the definition of semi-automatic labelling unit) but it can also be automatic by fitting the labelling unit with suitable means (automatic labelling unit).

The indicated steps are repeated until all the envisaged test tubes have been filled.

The procedure described above has the following advantages compared to current procedures:

Absolute guarantee of "chain of custody" maintenance, meaning guarantee of a correct and bi-univocal relationship between the patient and the containers of his/her biological products considering that said containers are produced at the same time as the patient identification process and their use, thereby avoiding any possibility of a "mismatch" operation,
speeding up of sampling procedure,
limited production of paper documents,
greater reliability of the expendable material labelling process needed for the use of the services offered to the patient. Such greater reliability to be understood as correct labelling of the containers without causing identification problems relating to the containers themselves during the course of execution of the clinical process,
Elimination of human errors as regards labelling containers not coherent with the colour of the caps defining the clinical path of the containers themselves.

The invention claimed is:

1. An apparatus for identifying a patient and marking laboratory test tubes associated with such patient during the sampling of biological material to be analysed, comprising:
    a portable hardware device for processing and storing the patient's data in a high-security way, able to associate the patient's personal and biometric details,
    a device for reading said portable hardware device and for the biometric identification of the patient,
    a personal computer interacting with an operator and linked to a computer network to exchange data by means of application software with a remote data storage means, and
    a computerized labeling unit for test tubes comprising a printer of bar codes on labels suitable for receiving print commands from said personal computer following a comparison performed between expected and detected test tubes housed in a positioning and identification device supported by said labeling unit, wherein said device comprises a presence sensor for detecting the presence of the test tube, a length sensor for detecting the length of the test tube and a colour sensor for detecting the colour of a cap of the test tube being supported by a housing having an extensible portion which adapts to test tubes of different lengths, said housing being mobile between a position for the replacement and the loading of a rolled belt for supporting the labels and an identification and labeling position of the test tube, said sensors being able to identify the dimensional characteristics of the test tubes and the colour of the relevant caps.

2. The apparatus as defined in claim 1, wherein the housing of the test tube is provided with a base portion with a window and with an extensible portion movable with respect to said base portion between a first position for housing a short test tube leaving the window closed and a second position for housing a long test tube leaving the window open.

3. The apparatus as defined by claim 1, wherein said device is able to print a label with a bar code which is coherent with the characteristics of the test tube identified by the sensors.

4. The apparatus as defined by claim 1, further comprising a smart card, complete with microprocessor.

5. The apparatus as defined by claim 1, further comprising a removable identification bracelet featuring a microprocessor with associated biometric data.

6. The apparatus as defined by claim 1, further comprising a non-removable identification bracelet.

7. The apparatus as defined by claim 1, wherein said printer is suitable for printing the following information:
   the sample of biological material,
   the patient,
   the tests to be performed, and
   the physical characteristics of the test tube according to the tests to be performed on it.

8. A computerized-labeling unit for laboratory test tubes comprising, a printer for printing bar codes on labels suitable for receiving commands from a personal computer following a comparison between expected and detected test tubes housed in a positioning and identification device, said device comprising a test tube presence sensor, a test tube length sensor and a colour sensor for detecting the colour of the cap of the test tube, said test tube being supported by a housing having an extensible portion which adapts to test tubes of different lengths, said housing being mobile between a position for the replacement and the loading of a rolled belt for supporting the labels and a position for identifying and labeling the test tube, said sensors being able to identify the dimensional characteristics of the test tubes and the colour of the relevant caps.

9. The apparatus as defined by claim 2, further comprising a smart card complete with a microprocessor.

10. The apparatus as defined by claim 3, further comprising a smart card complete with a microprocessor.

11. The apparatus as defined by claim 2, further comprising a removable identification bracelet featuring a microprocessor with associated biometric data.

12. The apparatus as defined by claim 3, further comprising a removable identification bracelet featuring a microprocessor with associated biometric data.

13. The apparatus as defined by claim 4, further comprising a removable identification bracelet featuring a microprocessor with associated biometric data.

14. The apparatus as defined by claim 2, further comprising a non-removable identification bracelet.

15. The apparatus as defined by claim 3, further comprising a non-removable identification bracelet.

16. The apparatus as defined by claim 4, further comprising a non-removable identification bracelet.

17. The apparatus as defined by claim 5, further comprising a non-removable identification bracelet.

18. The apparatus as defined by claim 2, wherein said printer is suitable for printing the following information:
   the sample of biological material,
   the patient,
   the tests to be performed, and
   the physical characteristics of the test tube according to the tests to be performed on it.

19. The apparatus as defined by claim 3, wherein said printer is suitable for printing the following information:
   the sample of biological material,
   the patient,
   the tests to be performed, and
   the physical characteristics of the test tube according to the tests to be performed on it.

\* \* \* \* \*